(12) United States Patent
Pujara et al.

(10) Patent No.: US 12,303,673 B2
(45) Date of Patent: May 20, 2025

(54) SYRINGE NEEDLE SHIELD

(71) Applicant: BECTON, DICKINSON AND COMPANY, Franklin Lakes, NJ (US)

(72) Inventors: Akshay Pujara, Parsippany, NJ (US); Jason Mondro, Deerfield Beach, FL (US); Kevin Watts, Kearney, NE (US); Roger Hoeck, Holdrege, NE (US); Lance Jacobi, Kearney, NE (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 1022 days.

(21) Appl. No.: 17/263,529

(22) PCT Filed: Jul. 23, 2019

(86) PCT No.: PCT/US2019/043027
§ 371 (c)(1),
(2) Date: Jan. 26, 2021

(87) PCT Pub. No.: WO2020/023506
PCT Pub. Date: Jan. 30, 2020

(65) Prior Publication Data
US 2021/0236740 A1 Aug. 5, 2021

Related U.S. Application Data

(60) Provisional application No. 62/711,101, filed on Jul. 27, 2018.

(51) Int. Cl.
*A61M 5/32* (2006.01)

(52) U.S. Cl.
CPC .................. *A61M 5/3202* (2013.01)

(58) Field of Classification Search
CPC ............ A61M 5/3202; A61M 25/0612; A61M 25/0618
See application file for complete search history.

(56) References Cited

U.S. PATENT DOCUMENTS

| 5,209,738 A | 5/1993 | Bruno |
| 5,451,213 A | 9/1995 | Teicher et al. |
| 5,483,973 A | 1/1996 | Benson et al. |
| 5,718,689 A | 2/1998 | Stevenson |
| D787,669 S | 5/2017 | Huang et al. |
| 10,512,733 B2 | 12/2019 | Roberts et al. |
| 2004/0097882 A1 | 5/2004 | DiBiasi et al. |

(Continued)

FOREIGN PATENT DOCUMENTS

| EP | 1138338 A1 | 10/2001 |
| JP | H06-190043 A | 7/1994 |

(Continued)

*Primary Examiner* — Dung T Ulsh
(74) *Attorney, Agent, or Firm* — Dickinson Wright, PLLC (57) ABSTRACT

A syringe needle shield (10) and a method of using the syringe needle shield (10) that is configured to enclose a needle (4) of a syringe (2), the syringe needle shield (10) comprising a proximal end (20) providing access to an inner cavity (50), a distal end (22) including a flange (30), and an outer surface (24) including a plurality of ribs (40) disposed adjacent to the flange (30), each of the plurality of ribs (40) including a substantially flat surface (42) and a concave surface (44), wherein the substantially flat surface (42) is adjacent to the concave surface (44).

14 Claims, 8 Drawing Sheets

(56) References Cited

U.S. PATENT DOCUMENTS

| | | | |
|---|---|---|---|
| 2007/0016146 A1 | 1/2007 | Yang | |
| 2010/0012537 A1* | 1/2010 | Farrar | B65D 77/046 |
| | | | 206/364 |
| 2012/0179114 A1* | 7/2012 | Yokota | A61M 5/343 |
| | | | 604/239 |
| 2014/0012206 A1* | 1/2014 | Shaw | A61B 5/150587 |
| | | | 604/198 |
| 2014/0305823 A1* | 10/2014 | Gelfand | A61B 5/15101 |
| | | | 600/583 |
| 2016/0220767 A1 | 8/2016 | Roberts et al. | |
| 2018/0318519 A1 | 11/2018 | Lee | |

FOREIGN PATENT DOCUMENTS

| | | |
|---|---|---|
| JP | HEI 06190043 A | 7/1994 |
| JP | H06-219483 A | 8/1994 |
| JP | HEI 06219483 | 8/1994 |
| JP | 2004-283554 A | 10/2004 |
| JP | 2013523204 A | 6/2013 |
| JP | 2013-533777 A | 8/2013 |
| WO | 2011117840 A2 | 3/2011 |
| WO | 2012000836 A1 | 1/2012 |
| WO | 2015028488 A1 | 3/2015 |

\* cited by examiner

SYRINGE NEEDLE SHIELD

CROSS-REFERENCE TO RELATED APPLICATION

This application claims priority under 35 U.S.C. 119 (e) to U.S. provisional application Ser. No. 62/711,101, filed on Jul. 27, 2018, and for the United States is a continuation-in-part of U.S. Design Application No. 29/658,132, filed on Jul. 27, 2018, both of which are incorporated herein by reference in their entirety.

FIELD OF THE INVENTION

The present invention relates to a shield for enclosing a needle of a syringe for use in medication delivery.

BACKGROUND OF THE INVENTION

Syringe needles are typically shielded to protect against accidental needle sticking and to ensure sterility. However, difficulties in use while ensuring safety and increasing manufacturing issues arise. Thus, an improved syringe needle shield is desired.

SUMMARY OF THE INVENTION

It is an aspect of the present invention to provide a syringe needle shield that is more ergonomically designed to provide improved grip and leverage. Such a configuration increases clinician performance by preventing slippage, reducing recoil effect and improving assembly after use (recapping). In addition, standard injection molding procedures can still be used.

The foregoing and/or other aspects of the present invention can be achieved by providing a shield that is configured to enclose a needle of a syringe, the shield comprising a proximal end providing access to an inner cavity, a distal end including a flange, and an outer surface including a plurality of ribs disposed adjacent to the flange, the plurality of ribs includes a substantially flat surface, and a concave surface, wherein the substantially flat surface is adjacent to the concave surface.

The foregoing and/or other aspects of the present invention can also be achieved by providing a method of using a shield and a syringe, the method comprising removing the shield enclosing a needle of the syringe, operating the syringe, disposing the shield vertically with an inner cavity of the shield oriented upwardly, inserting the needle of the syringe into the inner cavity of the shield, and depressing the syringe into the shield to secure and lock the shield to the syringe.

Additional and/or other aspects and advantages of the present invention will be set forth in the description that follows, or will be apparent from the description, or may be learned by practice of the invention.

BRIEF DESCRIPTION OF THE DRA WINGS

The above aspects and features of the present invention will be more apparent from the following description of an exemplary embodiment of the present invention with reference to the accompanying drawings, in which.

DETAILED DESCRIPTION OF EXEMPLARY EMBODIMENTS

Figure 1:
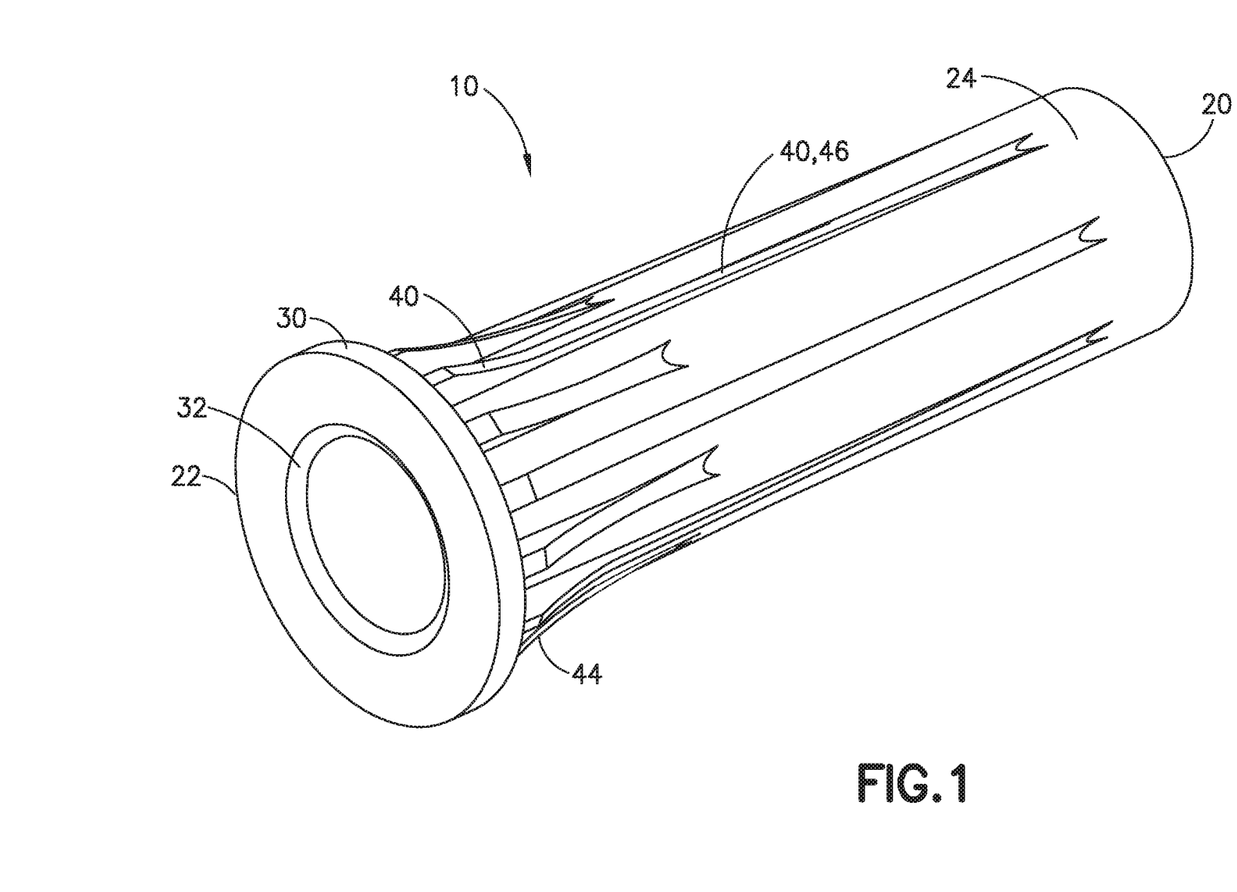
FIG. 1 illustrates a top perspective view of an embodiment of a syringe needle shield according to the present invention.
Figure 2:
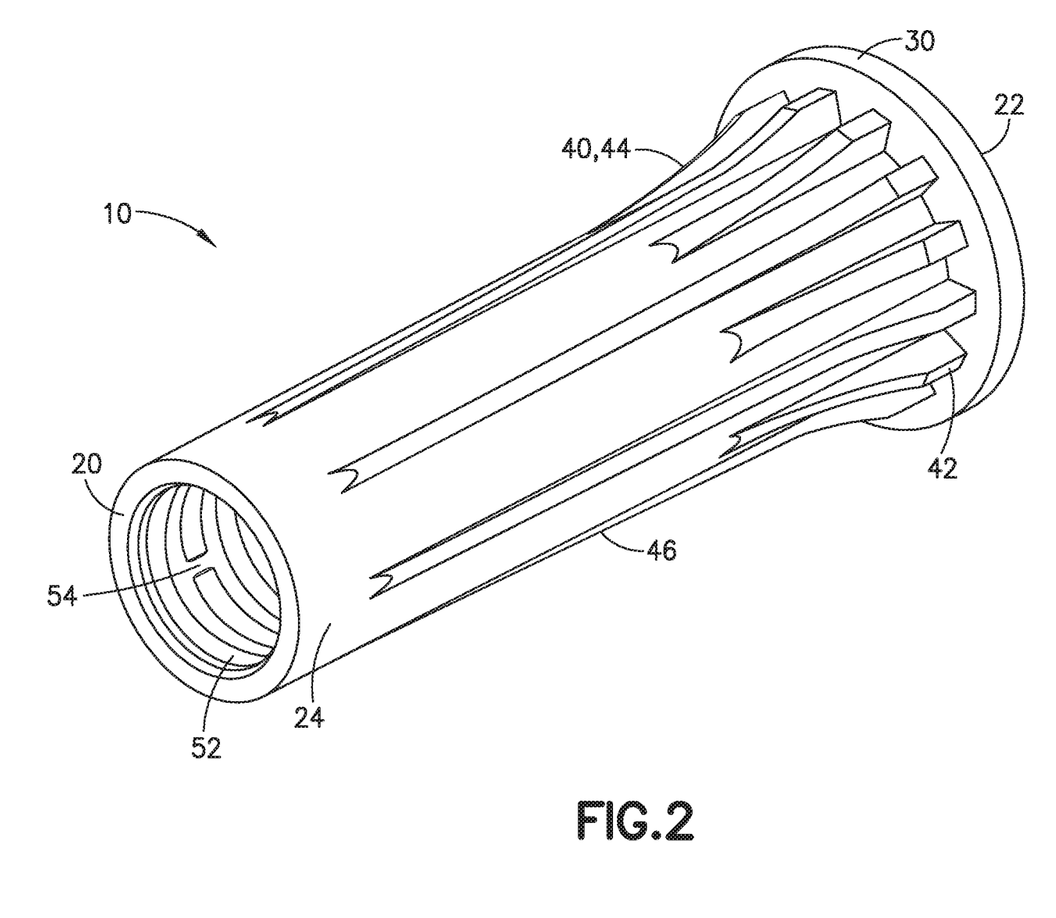
FIG. 2 is a bottom perspective view of the syringe needle shield shown in FIG. 1.
Figure 3:
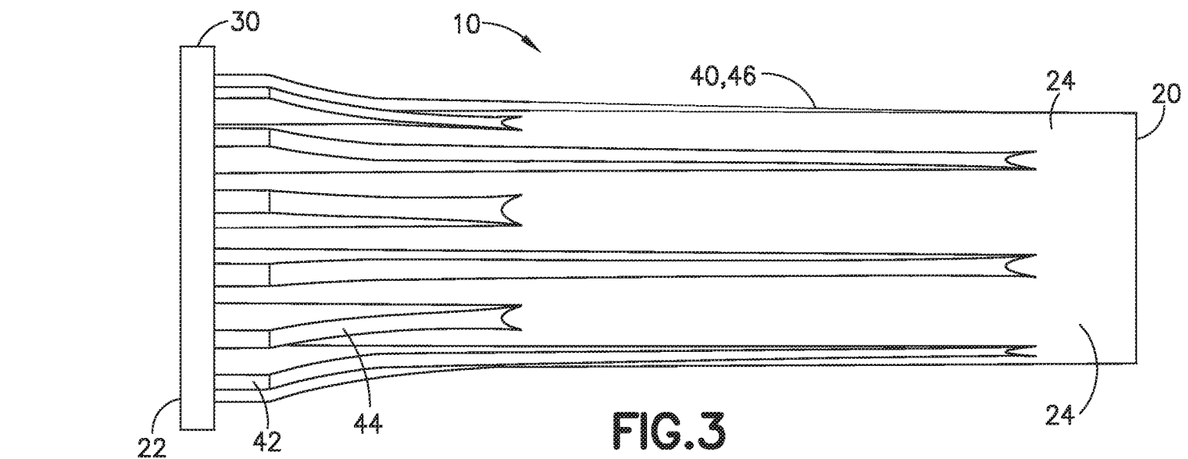
FIG. 3 is a top view of the syringe needle shield shown in FIGS. 1 and 2.
Figure 4:
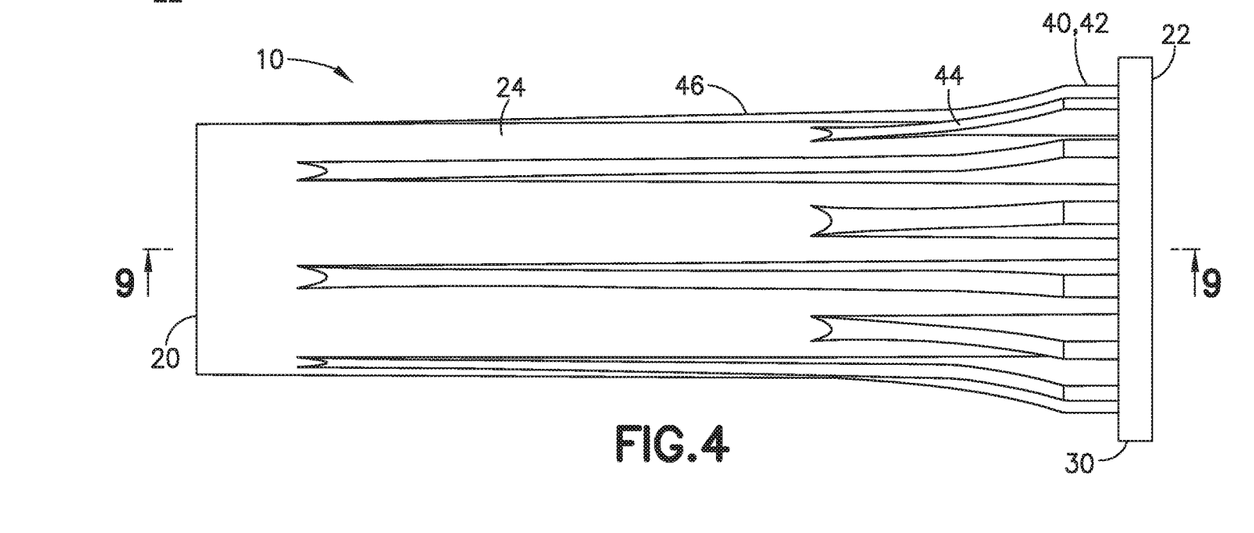
FIG. 4 is a bottom view of the syringe needle shield shown in FIGS. 1-3.
Figure 5:
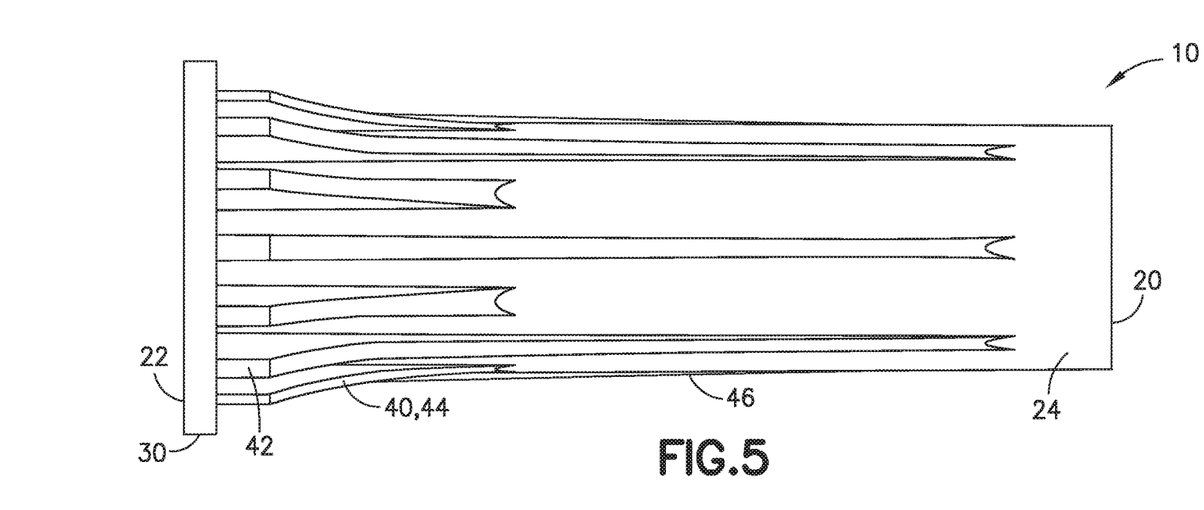
FIG. 5 is a side view of the syringe needle shield shown in FIGS. 1-4.
Figure 6:
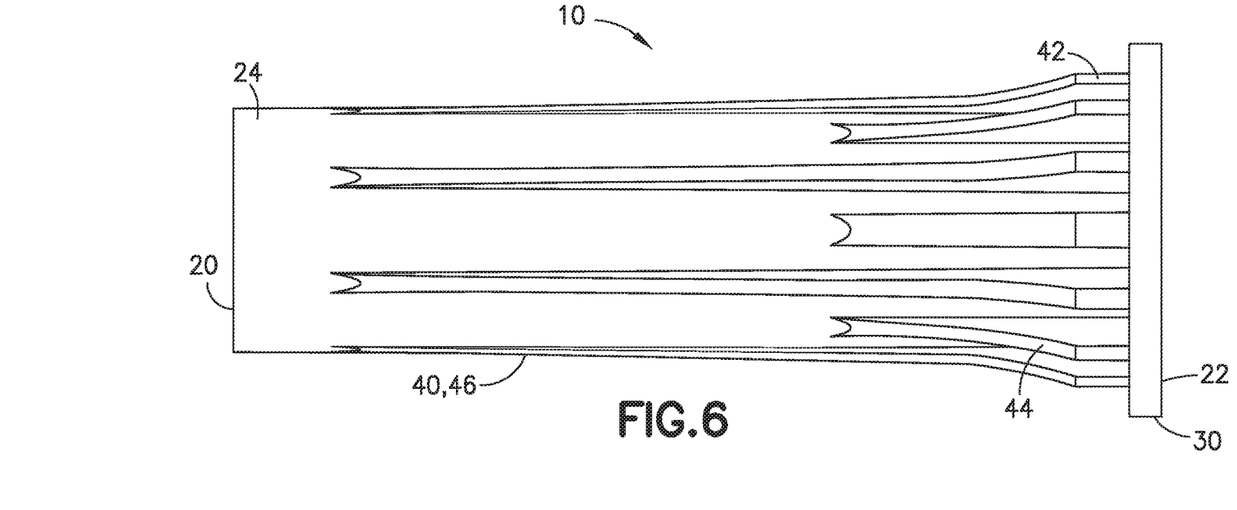
FIG. 6 is an opposite view of the syringe needle shield shown in FIGS. 1-5.
Figure 7:
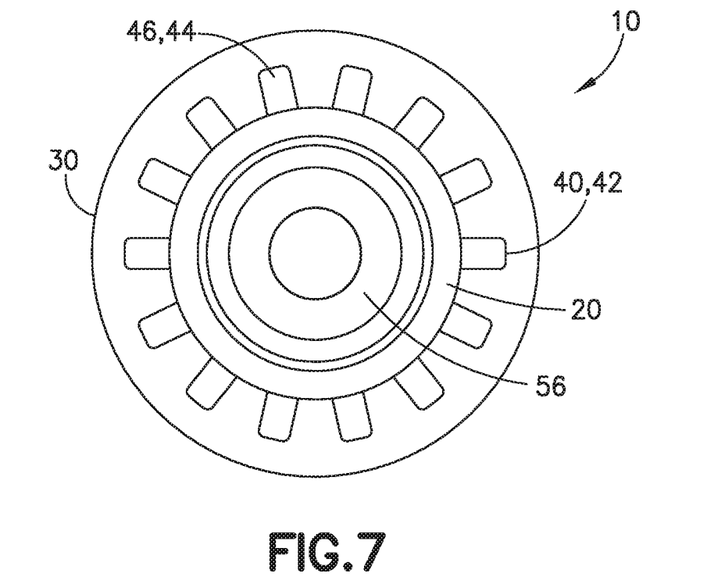
FIG. 7 is a front view of the syringe needle shield shown in FIGS. 1-6.
Figure 10:
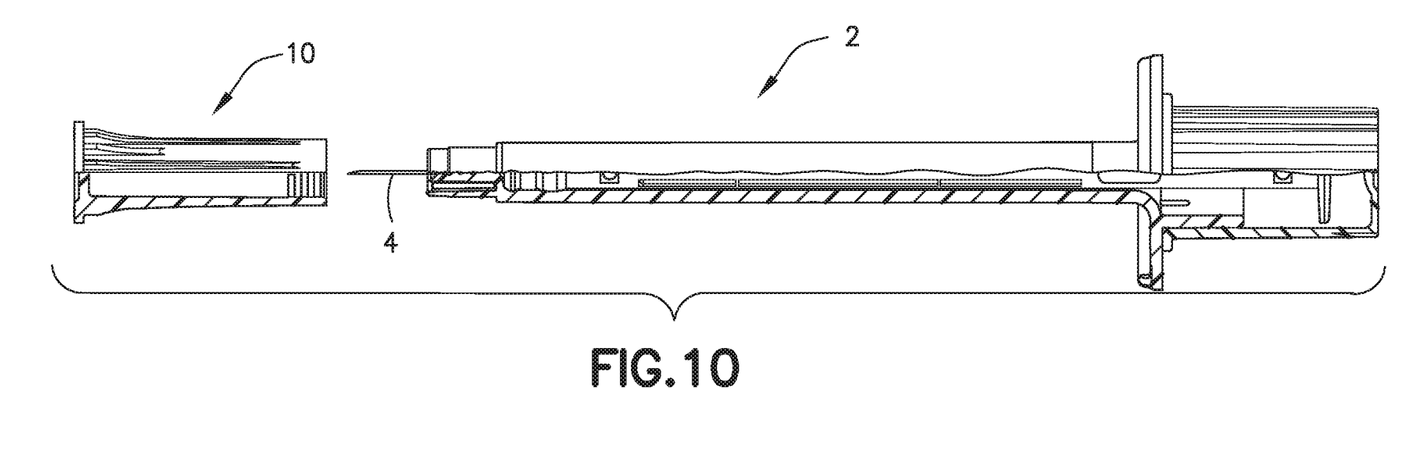
FIG. 10 is a disassembled view of the syringe needle shield of FIGS. 1-9 and a syringe.
Figure 11:
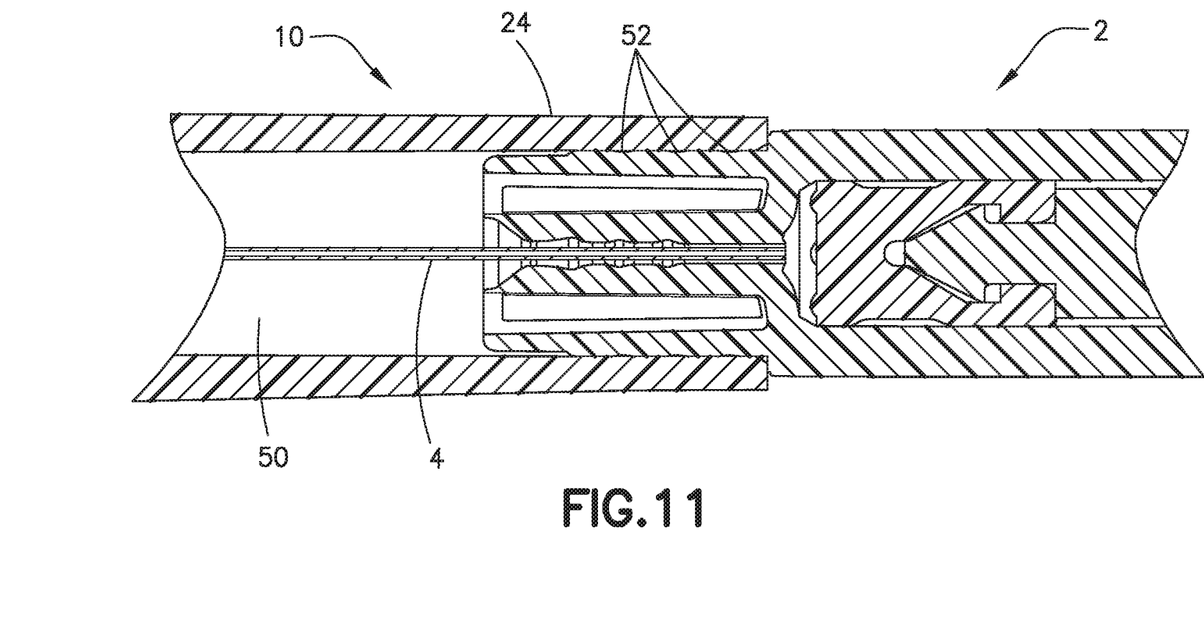
FIG. 11 is an assembled view of the syringe needle shield of FIGS. 1-9 and the syringe.

FIGS. 1 and 2 illustrate perspective views of a syringe needle shield 10 in accordance with an embodiment of the present invention. As illustrated in FIGS. 10 and 11, the shield 10 is configured to enclose a needle 4 of a syringe 2. The shield 10 is designed to be compatible with a variety of syringe sizes such as 0.3 ml, 0.5 ml and 1.0 ml syringes.

The shield 10 includes an open proximal end 20 and a closed distal end 22. Each of the proximal and distal ends 20, 22 is substantially flat and substantially perpendicular to a longitudinal axis of the shield 10. During reattachment to a syringe after use (recapping), the closed distal end 22 is configured to lie flat on a flat surface and allow the shield 10 to stand up vertically in a stable manner without tipping over. Such a configuration provides benefits in assembly and use as further described below.

The shield 10 also includes a cylindrical outer surface 24 that extends longitudinally to comprise a body of the shield 10. The cylindrical outer surface 24 provides a substantially uniform outer diameter and thickness for most of the length of the shield 10. Such a configuration advantageously provides stability and ergonomic use for the clinician.

A distal end 22 of the outer surface 24 includes a shallow depression 32 and a flange 30. That is, the cylindrical outer surface 24 extends along the length of the shield 10 until it reaches the flange 30. The flange 30 is substantially circular in shape and extends radially beyond the outer surface 24, as well as radially beyond a plurality of ribs 40 on the outer surface 24 as described below. That is, the diameter of the flange 30 is greater than the open proximal end 20 of the shield 10.

The closed distal end 22 of the shield 10 is also a distal surface of the flange 30. Accordingly, as described above, the distal surface of the flange 30 is substantially flat and substantially perpendicular to a longitudinal axis of the shield 10. The flange 30 advantageously provides a stopping surface for the clinician's fingers when removing the shield 10 from the syringe 2, i.e. during a pulling-away motion.

Figure 8:
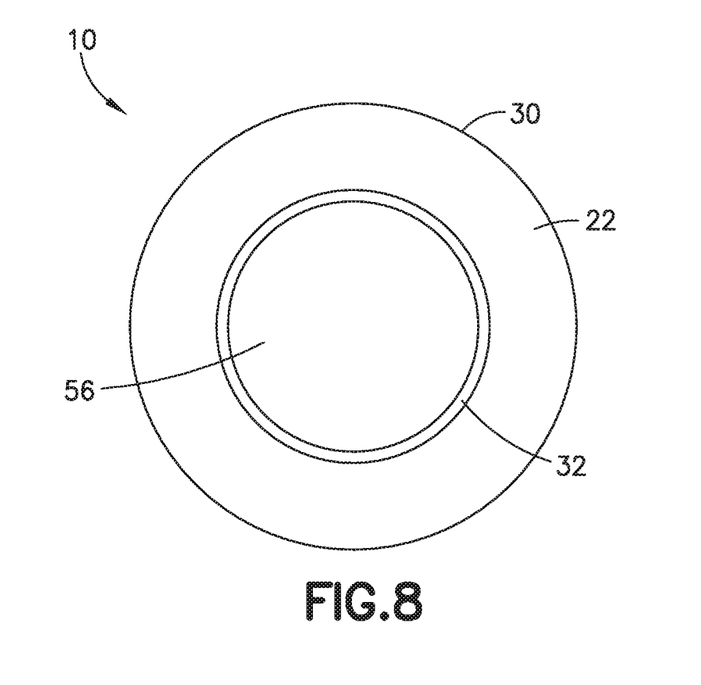
FIG. 8 is a rear view of the syringe needle shield shown in FIGS. 1-7.
Figure 9:
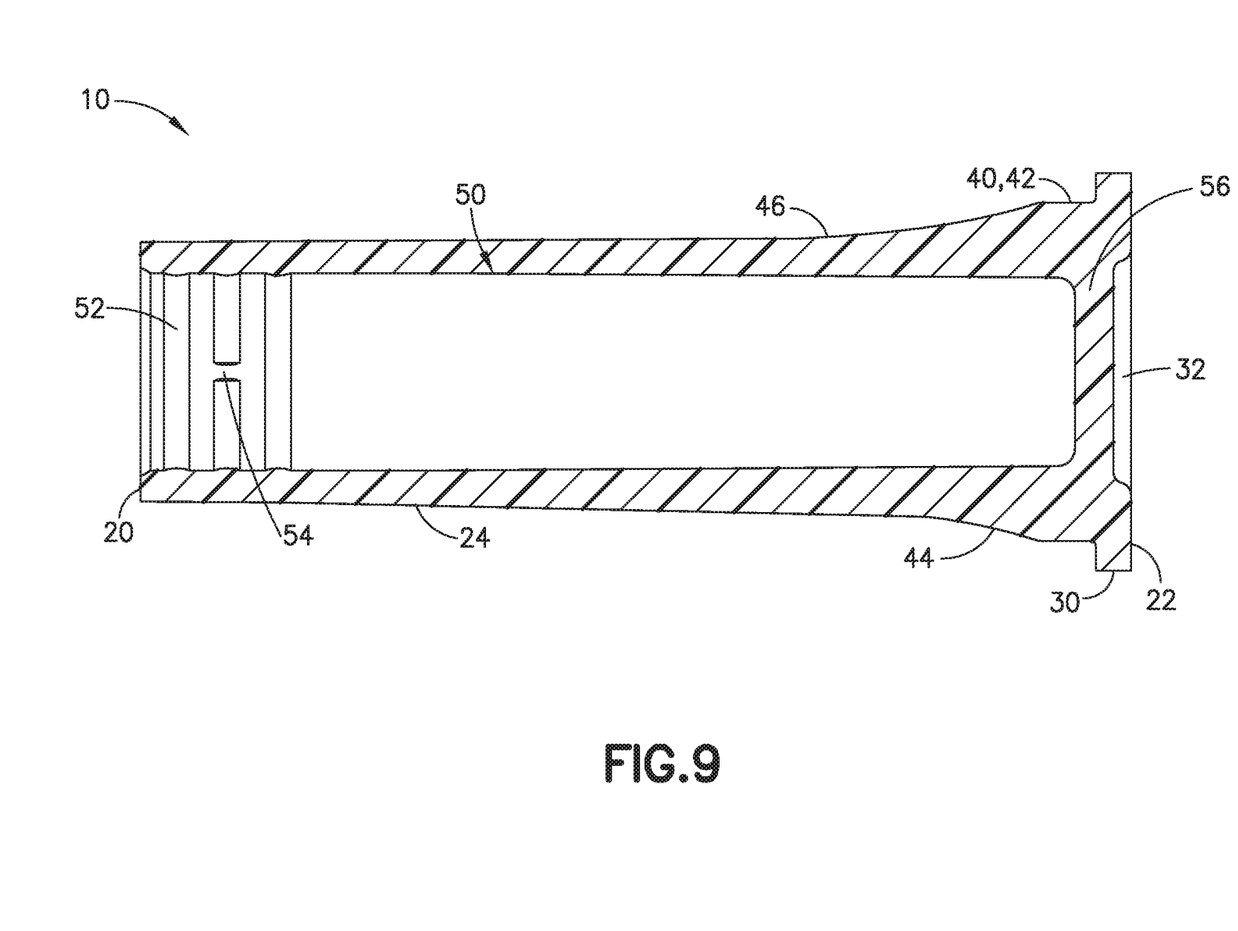
FIG. 9 is a cross sectional view of the syringe needle shield shown in FIGS. 1-8.

FIGS. 8 and 9 illustrate that the flange 30 includes the shallow depression 32. The depression 32 is an open external cavity on the closed distal end 22 and the distal surface of the flange 30. The depression 32 is internally separated from an inner cavity 50 of the shield 10 via an inner wall 56.

As illustrated in FIG. 11, the inner cavity 50 is formed by a hollow portion of the shield 10 that extends into the open proximal end 20. The inner cavity 50 is configured to enclose the needle 4 of the syringe 2 before and/or after use. FIG. 9 illustrates that the inner cavity 50 extends in a substantially uniform inner diameter from the inner wall 56 to the open proximal end 20 of the shield 10. Moreover, the open proximal end 20 provides access to the inner cavity 50 of the shield 10.

FIGS. 2 and 9 further illustrate interference rings 52 disposed at the open proximal end 20 of the shield 10 within the inner cavity 50. The interference rings 52 are configured to engage with the syringe 2, as illustrated in FIG. 11, to enclose the syringe needle 4 in the inner cavity 50. The interference rings 52 also provide a sealing surface when engaged to the syringe 2 to prevent contamination from entering or leaving the shield 10. Specifically, prior to needle 4 use, the shield 10 protects the syringe needle 4 from contamination. After needle 4 use, the shield 10 encloses the used needle 4 of the syringe 2 to prevent blood or any other bodily fluids on the needle 4 from spreading.

The interference rings 52 also include a tortuous path 54 via gaps in the interference rings 52. Sterility of the syringe 2 may be maintained by using the tortuous path 54 to prevent access to airborne microorganisms from the outside of the shield 10 into the inner cavity 50. That is, the tortuous path 54 provides sealing similar to a labyrinth seal and reduces the path of airflow. For example, sterility can be maintained by providing matching tortuous path faces on the shield 10 and on the syringe 2. Thus, the interference rings 52 provide a secure engagement to the syringe 2 and the tortuous path 54 provides sterility.

The combination of the interference rings 52 and the tortuous path 54 also provides an audible sound upon removal of the shield 10 from the syringe 2. The pitch of the sound changes depending on the speed of removal.

FIGS. 3-7 illustrate the plurality of ribs 40 on the outer surface 24 of the shield 10. The plurality of ribs 40 are thin protrusions substantially equally spaced circumferentially around the outer surface 24 of the shield 10 and adjacent to the flange 30 at the closed distal end 22 of the shield 10. Between the thin protrusions of the plurality of ribs 40 is the outer surface 24.

The height of the plurality of ribs 40 does not protrude beyond the outer diameter of the flange 30. However, the height of the plurality of ribs 40 increases the thickness defined by material between the outer surface 24 and the inner cavity 50. This advantageously provides increased stiffness and strength to the shield 10. The length of the plurality of ribs 40 extends in a direction substantially parallel to the longitudinal axis of the shield 10.

Each of the plurality of ribs 40 includes a substantially flat surface 42, a concave surface 44 and an extended portion 46. The flat surface 42 is a surface adjacent to the flange 30 that extends longitudinally as a substantially flat surface. The substantially flat surface 42 is substantially parallel to the central axis of the shield 10. The outer diameter of the flange 30 is greater than the outer diameter of the substantially flat surface 42. The substantially flat surface 42 is a portion of the plurality of ribs 40 that has the greatest thickness defined by material between the outer surface 24 and the inner cavity 50.

The concave surface 44 is adjacent to the flat surface 42 and decreases the height of the rib in a concave shape. Accordingly, the thickness defined by material between the outer surface 24 and the inner cavity 50 decreases as the concave surface 44 approaches the open proximal end 20. The concave surface 44 advantageously contours to the finger of the clinician to provide an ergonomically improved gripping surface during use. This concave surface 44 is especially advantageous because the plurality of ribs 40 are individually spaced apart from each other, with the outer diameter 44 in between, to achieve optimum gripping.

The extended portion 46 is adjacent to the concave surface 44. The extended portion 46 is angled so that the top surface of the angled portion 46 merges with the outer surface 24 of the shield 10. The extended portion 46 extends longitudinally to nearly the open proximal end 20 of the shield 10. The extended portion 46 is disposed on alternate ribs of the plurality of ribs 40. That is, only some of the ribs 40 includes an extended portion 46. Accordingly, the angled portions 46 of the plurality of ribs 40 have a thickness slightly greater than the thickness defined by the material between the outer surface 24 and the inner cavity 50. The extended portion 46 also advantageously provides more leverage for the clinician during use, especially during removal.

The plurality of ribs 40 advantageously provide friction for a clinician to hold on to and reduce slippage. Accordingly, the clinician is advantageously able to twist the shield 10. The increased friction also minimizes an unintended recoil movement that can be detrimental to the clinician. For example, unintended movement can lead to an accidental needle stick to the clinician. Thus, the clinician experiences a more accurate performance and a user-friendly experience via a pulling force and/or a twisting force by the clinician.

The plurality of ribs 40 also advantageously aids diabetes patients and other individuals who are not dexterous. Patients who are elderly or experience tremors also advantageously benefit from the plurality of ribs 40, specifically from the texture and the raised features resulting in improved handling.

Further, the shield 10 disclosed herein is advantageously simple in design which minimizes challenges in injection molding and processing. There are no undercuts and minimal changes in thicknesses throughout the shield 10. The geometry is not complex, thus reducing cost. Accordingly, standard injection molding procedures can advantageously be applied.

Moreover, the shape of the flange 30 and the plurality of tapered ribs 40 in the shield 10 allows for a gradual transition. This shape advantageously improves the assembly process since the flange 30 does not get stuck in a feeder system.

The shield 10 disclosed herein also provides advantages in use. In a traditional syringe 2 and shield assembly, both hands of a clinician are needed to enclose the needle 4. For example, during recapping of current syringe products prior to disposal, the shield is laid flat on a surface and the patient is expected to scoop up the shield with the tip of the syringe needle 4 and then use the second hand to secure the shield to the syringe. Accordingly, the risk of needle sticking is present during assembly. However, the shield 10 disclosed herein overcomes these problems.

To begin operation, the shield 10 is removed from the syringe 2 to uncover the needle 4 as illustrated in FIG. 10. The syringe 2 is now ready for operation such as medication delivery. After the syringe needle 4 is used, the clinician places the closed distal end 22 of the shield 10 on a flat surface so that the inner cavity 50 is disposed in an upward, vertical direction. The clinician then places the syringe needle 4 into the inner cavity 50 to enclose the syringe needle 4. Subsequently, as illustrated in FIG. 11, the clinician depresses the syringe 2 into the inner cavity 50 to engage, lock and seal the syringe 2 to the interference rings 52 and tortuous path 54 of the shield 10.

Since the shield 10 is able to be disposed in an upward, vertical direction on its own (in a stable state without tipping over), the clinician advantageously only needs to use one hand to engage the syringe 2 to the shield 10. Accordingly, such a configuration also advantageously improves safety as the risk of needle sticking is removed when the clinician uses only one hand. In other words, the second hand is not in harm's way (via an accidental needle stick during re-shielding).

The foregoing detailed description of an exemplary embodiment has been provided for the purpose of explaining the principles of the invention and its practical application, thereby enabling others skilled in the art to understand the invention for various embodiments and with various modifications as are suited to the particular use contemplated. This description is not necessarily intended to be exhaustive or to limit the invention to the precise embodiment disclosed. Any of the elements disclosed herein may be combined with one another in a different manner to form various additional embodiments not specifically disclosed. Accordingly, additional embodiments are possible and are intended to be encompassed within this specification and the scope of the invention. The specification describes a specific example to accomplish a more general goal that may be accomplished in other ways.

As used in this application, the terms "front," "rear," "upper," "lower," "upwardly," "downwardly," and other orientational descriptors are intended to facilitate the description of the exemplary embodiments of the present invention, and are not intended to limit the structure of the exemplary embodiments of the present invention to any particular position or orientation. Terms of degree, such as "substantially" or "approximately" are understood by those of ordinary skill to refer to reasonable ranges outside of the given value, for example, general tolerances associated with manufacturing, assembly, and use of the described embodiments.

The invention claimed is:

1. A syringe needle shield that is configured to enclose a needle of a syringe, the syringe needle shield comprising:
   a proximal end providing access to an inner cavity;
   a distal end including a flange; and
   an outer surface including a plurality of ribs extending radially from the outer surface and contacting the flange, each of the plurality of ribs including:
      a substantially flat surface parallel to a centerline of the syringe needle shield; and
      a concave surface, the substantially flat surface being adjacent to the concave surface.

2. The syringe needle shield of claim 1, wherein the flange is substantially circular in shape.

3. The syringe needle shield of claim 1, wherein the flange includes a depression on the distal end of the shield.

4. The syringe needle shield of claim 3, wherein the depression is internally separated from the inner cavity by an inner wall.

5. The syringe needle shield of claim 1, wherein a surface of the proximal end and a surface of the distal end are substantially flat and substantially perpendicular with respect to a longitudinal axis of the shield.

6. The syringe needle shield of claim 1, wherein the substantially flat surface of the plurality of ribs contacts the flange.

7. The syringe needle shield of claim 1, wherein an outer diameter of the flange is greater than an outer diameter of the substantially flat surface of the plurality of ribs.

8. The syringe needle shield of claim 1, wherein one or more of the plurality of ribs includes a plurality of extended portions angled to converge into the outer surface of the shield in a direction toward the proximal end.

9. The syringe needle shield of claim 8, wherein the plurality of extended portions is angled to converge into the outer diameter of the shield.

10. The syringe needle shield of claim 8, wherein the plurality of extended portions are alternately present on the plurality of ribs.

11. The syringe needle shield of claim 8, wherein at least one of the plurality of ribs does not include an extended portion.

12. The syringe needle shield of claim 1, further comprising an interference ring disposed on a proximal end of the inner cavity.

13. The syringe needle shield of claim 12, wherein the interference ring includes a tortuous path.

14. The syringe needle shield of claim 1, wherein the plurality of ribs extends in a direction substantially parallel to the longitudinal axis of the shield.

* * * * *